United States Patent [19]

Krüger et al.

[11] Patent Number: 5,371,271

[45] Date of Patent: Dec. 6, 1994

[54] PESTICIDAL SUBSTITUTED AMINOPHENYL CARBAMATES

[75] Inventors: Bernd-Wieland Krüger, Wuppertal; Klaus Sasse, Berg.-Gladbach; Peter Heitkämper, Dormagen; Klaus König, Odenthal; Wilhelm Brandes, Leichlingen; Gerd Hänssler; Albrecht Marhold, both of Leverkusen, all of Germany

[73] Assignee: Bayer Aktiengesellschaft, Leverkusen, Germany

[21] Appl. No.: 90,342

[22] Filed: Aug. 18, 1993

Related U.S. Application Data

[60] Division of Ser. No. 852,484, Mar. 16, 1992, Pat. No. 5,260,474, which is a continuation of Ser. No. 473,552, Feb. 1, 1990, abandoned, which is a division of Ser. No. 197,009, May 20, 1988, Pat. No. 4,939,170.

[30] Foreign Application Priority Data

Jun. 3, 1987 [DE] Germany ............................ 3718522
Feb. 12, 1988 [DE] Germany ............................ 3804288

[51] Int. Cl.$^5$ ...................... C07C 271/48; A01N 47/22
[52] U.S. Cl. ...................... 560/136; 549/372; 549/425; 560/29
[58] Field of Search ................ 560/136, 29; 549/372, 549/425; 514/490

[56] References Cited

U.S. PATENT DOCUMENTS

| | | | |
|---|---|---|---|
| 3,927,070 | 12/1975 | Szabo | 260/479 C |
| 4,229,208 | 10/1980 | Boroschowski et al. | 560/29 |
| 4,344,790 | 8/1982 | Boroschewski et al. | 71/111 |
| 4,939,170 | 7/1990 | Kruger et al. | 514/483 |
| 5,260,474 | 11/1993 | Kruger et al. | 560/25 |

FOREIGN PATENT DOCUMENTS

| | | |
|---|---|---|
| 0117024 | 8/1984 | European Pat. Off. . |
| 0125901 | 11/1984 | European Pat. Off. . |
| 0616654 | 4/1980 | Switzerland . |

OTHER PUBLICATIONS

Chemical Abstracts, vol. 108, No. 14, Apr. 4, 1988, Columbus, Ohio, USA.
Harada, Suketaka, "Preparation of m-aminophenol derivatives as materials for pharmaceuticals, and dyes", p. 701, col. 2/1, para. No. 131 277 & Jpn. Kokai Tokkyo Koho JP 62,212 353.

*Primary Examiner*—José G. Dees
*Assistant Examiner*—Barbara S. Frazier
*Attorney, Agent, or Firm*—Sprung Horn Kramer & Woods

[57] ABSTRACT

Fungicidal substituted aminophenyl carbamates of the formula

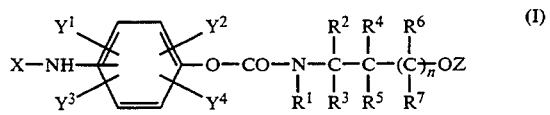

in which
X represents $-CO-NR^8R^9$; $-CO-OR^9$; $-CO-SR^9$; $-CO-R^{10}$; $-SO_2R^9$ or hydrogen, in which
$R^8$ represents hydrogen or alkyl,
$R^9$ represents optionally substituted aryl, optionally substituted aralkyl, optionally substituted alkyl, alkenyl, halogenoalkenyl, or in each case optionally substituted cycloalkyl, cycloalkenyl or cycloalkylalkyl, and $R^{10}$ has the meaning of $R^9$ or represents an optionally substituted heterocyclic ring,
$Y^1$ to $Y^4$ are identical or different and represent hydrogen, halogen, nitro, cyano, alkyl, halogenoalkyl, alkoxy, halogenoalkoxy, alkylthio, alkylsulfonyl or halogenolkylthio,
$R^1$ to $R^7$ are identical or different and represent hydrogen, alkyl, halogenoalkyl or alkoxyalkyl,
n represents 0 or 1, and
Z represents alkyl, halogenoalkyl or a

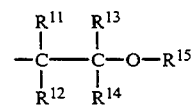

radical 6 Claims, No Drawings

PESTICIDAL SUBSTITUTED AMINOPHENYL CARBAMATES

This is a division of application Ser. No. 07/852,484, filed Mar. 16, 1992, now U.S. Pat. No. 5,260,474, which is a continuation of Ser. No. 07/473,552, filed Feb. 1, 1990, now abandoned, which is a division of Ser. No. 07/197,009, filed May 20, 1988, now U.S. Pat. No. 4,939,170.

The present invention relates to new aminophenyl carbamates, a process for the preparation thereof, and the use thereof for combating pests.

It has already been disclosed that certain substituted 3-aminophenyl carbamates have good herbicidal properties (cf. U.S. Pat. No. 3,832,389).

In addition, many phenyl carbamates which have a fungicidal action are known (cf. EP 116,409; EP t17,024 and EP 125,901).

Further substituted aminophenyl carbamates are described in human medicine (cf. JP 57,007,459).

New aminophenyl carbamates of the general formula

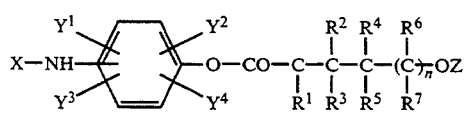

(I)

in which
X represents —CO—NR$^8$R$^9$; —CO—OR$^9$; —CO—SR$^9$; —CO—R$^{10}$; —SO$_2$R or hydrogen, in which
R$^8$ represents hydrogen or alkyl,
R$^9$ represents optionally substituted aryl, optionally substituted aralkyl, optionally substituted alkyl, alkenyl, halogenoalkenyl, or in each case optionally substituted cycloalkyl, cycloalkenyl or cycloalkylalkyl, and
R$^{10}$ has the meaning of R$^9$ or represents an optionally substituted heterocyclic ring,
Y$^1$ to Y$^4$ are identical or different and represent hydrogen, halogen, nitro, cyano, alkyl, halogenoalkyl, alkoxy, halogenoalkoxy, alkylthic, alkylsulfonyl or halogenalkylthio,
R$^1$ to R$^7$ are identical or different and represent hydrogen, alkyl, halogenoalkyl or alkoxyalkyl,
n represents 0 or 1, and
Z represents alkyl, halogenoalkyl or a

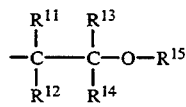

radical, in which
R$^{11}$ to R$^{14}$ are identical or different and represent hydrogen, alkyl, halogenoalkyl or alkoxyalkyl, and
R$^{15}$ represents alkyl, alkoxyalkyl or halogenoalkyl, have been found.

The substituted aminophenyl carbamates of the formula (I) contain one or more centers of asymmetry and can thus consist of diastereomers or mixtures of diastereomers, which are produced in different amount ratios. They are produced mainly as racemates.

It has furthermore been found that the new substituted aminophenyl carbamates of the formula (I)

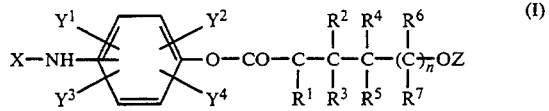

(I)

which
X represents —CO—NR$^8$R$^9$; —CO—OR$^9$; —CO—SR$^9$; —CO—R$^{10}$; —SO$_2$R$^9$ or hydrogen, in which
R$^8$ represents hydrogen or alkyl,
R$^9$ represents optionally substituted aryl, optionally substituted aralkyl, optionally substituted alkyl, alkenyl, halogenoalkenyl, or in each case optionally substituted cycloalkyl, cycloalkenyl or cycloalkylalkyl, and
R$^{10}$ has the meaning of R or represents an optionally substituted heterocyclic ring,
Y$^1$ to Y$^4$ are identical or different and represent hydrogen, halogen, nitro, cyano, alkyl, halogenoalkyl, alkoxy, halogenoalkoxy, alkylthio, alkylsulfonyl or halogenoalkylthio,
R$^1$ to R$^7$ are identical or different and represent hydrogen, alkyl, halogenoalkyl or alkoxyalkyl,
n represents 0 or 1, and
Z represents alkyl, halogenoalkyl or a

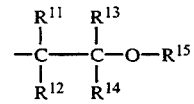

radical, in which
R$^{11}$ to R$^{14}$ are identical or different and represent hydrogen, alkyl, halogenoalkyl or alkoxyalkyl, and
R$^{15}$ represents alkyl, alkoxyalkyl or halogenoalkyl, are obtained when aminophenols of the formula (II)

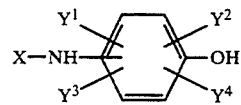

(II)

in which
X and Y$^1$ to Y$^4$ have the abovementioned meanings,
a) are reacted with isocyanates of the formula (III)

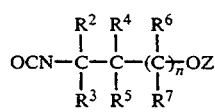

(III)

in which
R$^2$ to R$^7$, n and Z have the abovementioned meanings, appropriate in the presence of a base and if appropriate in the presence of diluents or solvents,
b) are reacted with halogenocarbonyl compounds of the formula (IV)

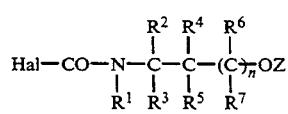

(IV)

in which $R^1$ to $R^7$, n and Z have the abovementioned meanings, and Hal represents halogen, preferably chlorine, if appropriate in the presence of an acid acceptor and if appropriate in the presence of a solvent or diluent.

It has further been found that the substituted aminophenyl carbamates of the formula (I) have a good action against pests, above all a high fungicidal activity. The new compounds can also be used in synergistic mixtures together with other known, highly active compounds.

Surprisingly, the aminophenyl carbamates of the formula (I) according to the invention exhibit, inter alia, a stronger fungicidal action than known compounds which are similar compounds with respect to their action and/or chemically.

In the context of the present invention, the substituents generally have the following meanings:

Halogen, everywhere where not otherwise stated, can denote fluorine, chlorine, bromine and iodine, preferably fluorine, chlorine and bromine.

Optionally substituted alkyl generally represents a straight-chain or branched hydrocarbon radical having 1 to 20 carbon atoms, preferably having 1 to 18 carbon atoms. Examples which may be mentioned are methyl, ethyl, n- and iso-propyl, n-, sec.-, iso- and tert.-butyl, hexyl, heptyl, dodeyl and octadecyl.

Substituents of an alkyl radical which may be mentioned as examples are halogen, as defined above, in addition alkoxy and alkylthio.

Alkoxy and alkylthio and alkylsulfonyl generally have a straight-chain or branched hydrocarbon radical which has 1 to 6, preferably 1 to 4, and particularly preferably 1 or 2, carbon atoms in the alkoxy or alkylthio or alkylsulfonyl part and which is bonded via oxygen, sulfur or $SO_2$ respectively.

Examples of substituted alkyl radicals which may be mentioned are: fluoromethyl, chloromethyl, bromomethyl, fluoroethyl, chloroethyl, bromoethyl, fluoropropyl, chloropropyl, bromopropyl, fluorobutyl, chlorobutyl, bromobutyl, fluoroisopropyl, chloroisopropyl, bromoisopropyl, difluoromethyl, trifluoromethyl, dichloromethyl, trichloromethyl, difluoroethyl, dichloroethyl, trifluoroethyl, tetrafluoroethyl, difluorobutyl, dichlorobutyl, trichloroethyl and trifluoropropyl. Very particularly preferred are trifluoromethyl, 1-fluoro-2-fluoromethyl-prop-2-yl and 1-chloro-2-methyl-prop-2-yl. Furthermore methoxymethyl, methoxyethyl, methoxypropyl, methoxybutyl, methoxypentyl, ethoxymethyl, ethoxyethyl, ethoxypropyl, ethoxybutyl, ethoxypentyl, propoxymethyl, propoxyethyl, propoxypropyl, propoxybutyl, propoxypentyl, butoxymethyl, butoxyethyl, butoxypropyl, butoxybutyl and butoxypentyl. Particularly preferred is 2-methoxyprop-2-yl.

Furthermore methylthiomethyl, methylthioethyl, methylthiopropyl, methylthiobutyl, methylthiopentyl, ethylthiomethyl, ethylthioethyl, ethylthiopropyl, ethylthiobutyl, ethylthiopentyl, propylthiomethyl, propylthioethyl, propylthiopropyl, propylthiobutyl, propylthiopentyl, butylthiomethyl, butylthioethyl, butylthiopropyl, butylthiobutyl and butylthiopentyl, methylsulfonyl, ethylsulfonyl and propylsulfonyl.

Alkyl, alkoxy and alkoxyalkyl represent a radical which has 1 to 6, preferably 1 to 4, carbon atoms per alkyl unit. Examples are shown hereinabove.

Halogenoalkoxy and halogenoalkylthio generally represent a straight-chain or branched hydrocarbon radical which has 1 to 6 carbon atoms and 1 to 9 identical or different halogen atoms and which is bonded via oxygen or sulfur respectively. Preferred radicals are these having 1 to 4 carbon atoms and 1 to 5 identical or different halogen atoms. Very particularly preferred radicals are those having 1 or 2 carbon atoms and 1 to 3 identical or different halogen atoms. Examples which may be mentioned are trifluoromethoxy, trichloromethoxy, difluorochloromethoxy, dichlorofluoromethoxy, difluoroethoxy, trifluoroethoxy, tetrafluoroethoxy, pentafluoroethoxy, trifluoromethylthio, trichloromethylthio, difluorochloromethylthio, dichlorofluoromethylthio, difluoroethylthio, trifluoromethylthio and tetrafluoroethylthio.

Halogenoalkyl in meaning to halogenoalkoxy.

Alkenyl generally represents a straight-chain or branched hydrocarbon radical having 2 to 16 carbon atoms and one or more, preferably one or two, double bonds. Lower alkenyl having 2 to 10 carbon atoms and one double bond is preferred. An alkenyl radical having 2 to 4 carbon atoms and one double bond is particularly preferred. Examples which may be mentioned are vinyl, allyl, propenyl, isopropenyl, butenyl, isobutenyl, pentenyl, isopentenyl, hexenyl, isohexenyl, heptenyl, isoheptenyl, octenyl and isooctenyl.

Halogenoalkenyl generally represents straightchain or branched alkyl having 1 to 6 carbon atoms and one or more identical or different halogen atoms and having one or more double bonds. Preferred radicals are those having 1 to 4 carbon atoms, 1 to 4 identical or different halogen atoms and one double bond. Examples which may be mentioned are 2,2-dichlorovinyl and 1,2,2-trichlorovinyl.

Aryl can represent an aromatic hydrocarbon radical having 6 to 12 carbon atoms. Examples which may be mentioned are phenyl, naphthyl and biphenyl. Phenyl is preferred.

Aralkyl can represent a radical having 7 to 18 carbon atoms, it being possible for a straight-chain or branched alkyl radical having 1 to 6, preferably 1 to 4, carbon atoms to be substituted by an aromatic radical having 6 to 12, preferably 6, carbon atoms. Examples which may be mentioned are benzyl, phenylethyl and phenylpropyl. Benzyl is preferred.

The aryl and aralkyl radicals may optionally be monosubstituted or polysubstituted by identical or different substituents. Substituents which may be mentioned as examples are halogen, alkyl having 1 to 6 carbon atoms, alkoxy having 1 to 6 carbon atoms, alkylthio having 1 to 6 carbon atoms, halogenoalkyl having 1 to 6 carbon atoms and 1 to 9 identical or different halogen atoms, halogenoalkoxy having 1 to 6 carbon atoms and 1 to 9 identical or different halogen atoms, halogenoalkylthio having 1 to 6 carbon atoms and 1 to 9 identical or different halogen atoms, cyano and nitro. These radicals have the preferred and particularly preferred meaning as already described above.

Cycloalkyl generally represents a cyclic hydrocarbon radical having 3 to 10 carbon atoms. The cyclopropyl, cyclopentyl and cyclohexyl radicals are preferred. Examples which may be mentioned are cyclopropyl, cyclobutyl, cyclopentyl, cyclohexyl and cyclodecanyl.

Cycloalkyl-alkyl can represent a radical having 4 to 20 carbon atoms, it being possible for a straightchain or branched alkyl radical having 1 to 10 carbon atoms to be substituted by a cycloalkyl radical having 3 to 10 carbon atoms. Examples which may be mentioned are cyclopropylmethyl, cyclopentylmethyl, cyclohexylmethyl, 1-cyclohexylethyl, 2-cyclohexylethyl, cycloheptylmethyl and 2-cycloheptylethyl.

The cycloalkyl and cycloalkyl-alkyl radicals may be monosubstituted or polysubstituted by identical or different substituents. Substituents which may be mentioned as examples are halogen, alkyl having 1 to 6 carbon atoms and halogenoalkyl having 1 to 6 carbon atoms and 1 to 9 identical or different halogen atoms. The substituents have the preferred and particularly preferred meaning which has already been given further above for the radicals.

Cycloalkenyl can represent a cyclic hydrocarbon radical having 5 to 10 carbon atoms and having one or more double bonds. Radicals having 5 or 6 carbon atoms and one double bond are preferred. The cycloalkenyl radical may be monosubstituted or polysubstituted by identical or different alkyl having 1 to 6 carbon atoms. The preferred and particularly preferred definition of the alkyl radical corresponds to that which is given above.

Heterocyclic ring can represent a radical having 5 to 7 ring members, preferably having 5 or 6 ring members, one or more hetero atoms, such as oxygen, sulphur or nitrogen, being included in addition to carbon, 5- or 6-membered rings having one or two oxygen atoms are preferred. Examples which may be mentioned are oxolanyl, oxanyl, dioxolanyl and dioxanyl. The heterocyclic rings may be monosubstituted or polysubstituted by identical or different alkyl having 1 to 6, preferably 1 to 4 and particularly preferably 1 or 2, carbon atoms. Examples which may be mentioned are: 2-methyl-oxolan-2-yl, 2-methyl-oxan-2-yl, 5-methyl-1,3-dioxolan-5-yl, 2-ethyl-oxolan-2-yl, 2 -ethyl-oxan-2-yl and 5-ethyl-1,3-dioxolan-5-yl.

Formula (I) provides a general definition of the substituted aminophenyl carbamates according to the invention. Preferred compounds of the formula (I) are those
in which
X represents —CO—NR$^8$R$^9$; —CO—OR$^9$; —CO—SR$^9$; —CO—R$^{10}$; —SO$_2$R$^9$ or hydrogen, in which R$^8$ represents hydrogen on straight-chain or branched alkyl having 1 to 6 carbon atoms, R$^9$ represents aryl having 6 to 12 carbon atoms, aryl having 6 to 12 carbon atoms which is monosubstituted to hexasubstituted by identical or different substituents from the series comprising halogen, alkyl having 1 to 6 carbon atoms, alkoxy having 1 to 6 carbon atoms, alkylthio having 1 to 6 carbon atoms, halogenoalkyl having 1 to 6 carbon atoms and 1 to 9 identical or different halogen atoms, halogenoalkoxy having 1 to 6 carbon atoms and 1 to 9 identical or different halogen atoms, halogenoalkylthio having 1 to 6 carbon atoms and 1 to 9 identical or different halogen atoms, cyano and nitro; furthermore represents aralkyl having 6 to 12 carbon atoms in the aryl part and having 1 to 6 carbon atoms in the straight-chain or branched alkyl part, it being possible for the aryl radical to be monosubstituted to hexasubstituted by identical or different substituents from the series comprising the abovementioned aryl substituents; furthermore represents straight-chain or branched alkyl having 1 to 20 carbon atoms; furthermore represents alkyl having 1 to 20 carbon atoms which is monosubstituted to tetrasubstituted by identical or different substituents from the series comprising halogen, alkoxy having 1 to 6 carbon atoms and alkylthio having 1 to 6 carbon atoms, it being possible for each of the alkyl parts to be straight-chain or branched; in addition represents straight-chain or branched alkenyl having 2 to 16 carbon atoms or alkenyl having 2 to 6 carbon atoms which is monosubstituted to hexasubstituted by identical or different halogen; in addition represents cycloalkyl having 3 to 10 carbon atoms or cycloalkylalkyl having 1 to 10 carbon atoms in the straight-chain or branched alkyl part and 3 to 10 carbon atoms in the cycloalkyl part, it being possible for the cyclic parts, in each case independently, to be monosubstituted to hexasubstituted by identical or different substituents from the series comprising halogen, straight-chain or branched alkyl having 1 to 6 carbon atoms and halogenoalkyl having 1 to 6 carbon atoms and 1 to 9 identical or different halogen atoms, or R$^9$, in addition, represents cycloalkenyl which has 5 to 10 carbon atoms and which may be monosubstituted to hexasubstituted by identical or different, straight-chain or branched alkyl having 1 to 6 carbon atoms;

R$^{10}$ has the meaning of R$^9$ or represents a heterocyclic ring having 5 to 7 ring members, one or more hetero atoms being included in addition to carbon. The heterocyclic ring may be monosubstituted to hexasubstituted by identical or different, straight-chain or branched alkyl having 1 to 6 carbon atoms;

Y$^1$ to Y$^4$ are identical or different and represent hydrogen, halogen, nitro, cyano, straight-chain or branched alkyl having 1 to 6 carbon atoms, halogenoalkyl having 1 to 6 carbon atoms in the straight-chain or branched alkyl part and 1 to 9 identical or different halogen atoms, alkoxy, halogenoalkoxy, alkylthio, alkylsulfopyl or halogenoalkylthio in each case having 1 to 6 carbon atoms in the straight-chain or branched alkyl part: and, if appropriate, 1 to 9 identical or different halogen atoms;

R$^1$ to R$^7$ are identical or different and represent hydrogen, straight-chain or branched alkyl having 1 to 6 carbon atoms, halogenoalkyl having 1 to 6 carbon atoms in the straight-chain or branched alkyl part and 1 to 9 identical or different halogen atoms, or alkoxyalkyl having 1 to 6 carbon atoms in each straight-chain or branched alkyl part;

n represents 0 or 1, and

Z represents straight-chain or branched alkyl or halogenoalkyl each having 1 to 6 carbon atoms and, if appropriate, 1 to 9 identical or different halogen atoms, or the

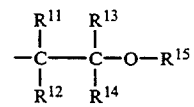

radical, in which

R$^{11}$ to R$^{14}$ are identical or different and represent hydrogen, straight-chain or branched, alkyl having 1 to 6 carbon atoms, halogenoalkyl having 1 to 6 carbon atoms in the straight-chain or branched alkyl part and 1 to 9 identical or different halogen atoms, or alkoxyalkyl having 1 to 6 carbon atoms each straight-chain or branched alkyl part, and R$^{15}$ represents straight-chain or branched alkyl, alkoxyalkyl or halogenoalkyl each having 1 to 6 carbon atoms in each alkyl part and, if appropriate, 1 to 9 identical or different halogen atoms.

Particularly preferred compounds of the formula (I) are those in which

X represents —CO—NR⁸R⁹; —CO—OR⁹; —CO—R¹⁰; —SO₂R⁹ or hydrogen, in which

R⁸ represents hydrogen,

R⁹ represents phenyl, benzyl, phenylethyl or 1-phenyl-1-methylethyl each of which is optionally monosubstituted, disubstituted or trisubstituted in the phenyl part by identical or different substituents from the series comprising halogen, straight-chain or branched alkyl having 1 to 4 carbon atoms, straight-chain or branched alkoxy having 1 to 4 carbon atoms, straight-chain or branched alkylthio having 1 to 4 carbon atoms, halogenoalkyl, halogenoalkoxy or halogenoalkylthio in each case having 1 to 4 carbon atoms in the straight-chain or branched alkyl part and 1 to 5 identical or different halogen atoms, cyano or nitro; represents straight-chain or branched alkyl having 1 to 18 carbon atoms; alkyl which has 1 to 4 carbon atoms in the straight-chain or branched alkoxy or alkylthio part and 1 to 10 carbon atoms in the alkyl part and which is monosubstituted, disubstituted or trisubstituted by identical or different substituents from the series comprising halogen, alkoxy or alkylthio; straight-chain or branched alkenyl having 2 to 8 carbon atoms; straight-chain or branched alkenyl having 2 to 4 carbon atoms which is monosubstituted, disubstituted or trisubstituted by identical or different halogen; cycloalkyl which has 3 to 6 carbon atoms or cycloalkyl-alkyl which has 3 to 6 carbon atoms in the cycloalkyl part and 1 to 6 carbon atoms in the straight-chain or branched alkyl part and each of which is optionally monosubstituted, disubstituted or trisubstituted by identical or different substituents from the series comprising halogen, straight-chain or branched alkyl having 1 to 4 carbon atoms or straight-chain or branched halogenoalkyl having 1 to 4 carbon atoms and 1 to 5 identical or different halogen atoms:

R¹⁰ has the meaning of R⁹ or represents a 5- or 6-membered heterocyclic ring which contains one or two oxygen atom sandwhich is optionally monosubstituted, disubstituted or trisubstituted by straight-chain or branched alkyl having 1 to 4 carbon atoms, Y¹ to Y⁴ are identical or different and represent hydrogen, halogen, straight-chain or branched alkyl having 1 to 4 carbon atoms, straight-chain or branched alkoxy or alkylsulfonyl having 1 to 4 carbon atoms in each alkyl part, or halogenoalkyl having 1 to 4 carbon atom in the straight-chain or branched alkyl part and 1 to 5 identical or different halogen atoms;

R¹ to R⁷ are identical or different and represent hydrogen or straight-chain or branched alkyl having 1 to 6 carbon atoms, n represents 0, and Z represents straight-chain or branched alkyl or halogenoalkyl each having 1 to 4 carbon atoms and, if appropriate, 1 to 5 identical or different halogen atoms, or the

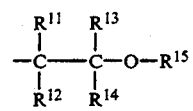

radical, in which

R¹¹ to R¹⁴ are identical or different represent hydrogen, straight-chain or branched alkyl or halogenoalkyl in each case having 1 to 4 carbon atoms and, if appropriate, 1 to 5 identical or different halogen atoms and R¹⁵ represents straight-chain or branched alkyl, alkoxyalkyl or halogenoalkyl in each case having 1 to 4 carbon atoms in each alkyl part and, if appropriate, 1 to5 identical or different halogen atoms.

Very particularly preferred compounds of the formula (I) are those in which

X represents —CO—NHR⁹; —CO—OR⁹; —CO—R¹⁰ or —SO₂R⁹, in which

R⁹ represents phenyl which is optionally monosubstituted, disubstituted or trisubstituted by identical or different substituents from the series comprising methyl, ethyl, methoxy, ethoxy, trichloromethyl, trifluoromethyl, trichloromethoxy, trifluoromethoxy, fluorine and chlorine; represents benzyl; straight-chain or branched alkyl having 1 to 5 carbon atoms; halogenoalkyl having 1 to 4 carbon atoms and 1 or 2 chlorine or fluorine atoms; halogenoalkenyl having 2 or 3 carbon atoms and 1 to 4 chlorine atoms; cyclopropyl or cyclohexyl each of which is optionally monosubstituted, disubstituted or trisubstituted by identical or different, straight-chain or branched alkyl having 1 to 4 carbon atoms, R¹⁰ represents straight-chain or branched alkyl having 1 to 18 carbon atoms, represents phenyl, cyclopropyl or cyclohexyl each of which is optionally monosubstituted, disubstituted or trisubstituted by identical or different substituents from the series comprising methyl, ethyl, n-propyl, iso-propyl, chlorine or trifluoromethyl; phenylalkyl which has 1 to 3 carbon atoms in the straight-chain or branched alkyl part and which is optionally monosubstituted or disubstituted by chlorine; straight-chain or branched halogenoalkyl having 1 to 4 carbon atoms and 1 or 2 chlorine or fluorine atoms; straight-chain or branched halogenoalkenyl having 2 to 4 carbon atoms and 1 to 4 identical or different halogen atoms, such as chlorine and fluorine, or oxanyl or oxolanyl or dioxanyl or dioxolanyl each of which is optionally monosubstituted by methyl or ethyl;

Y¹ to Y⁴ are identical or different and represent hydrogen, chlorine, fluorine, bromine, methyl or trifluoromethyl, R¹ to R⁷ are identical or different and represent hydrogen or methyl, n represents 0, and Z represents straight-chain or branched alkyl having 1 to 4 carbon atoms, or the

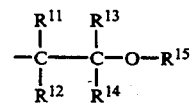

radical, in which $R^{11}$ to $R^{14}$ represent hydrogen, and $R^{15}$ represents methyl, ethyl, propyl, butyl methoxyethyl or ethoxyethyl.

In the compounds the amino group is in the 2-, 3- or 4-position, particularly preferably in the 3- or 4-position and very particularly preferably in 4-position to the carbamate radical.

If, for example, 2,6-dichloro-4-(tert.-butylcarbonylamino)-phenol and 2-methoxyethyl isocyanate are used as starting materials, the course of the reaction of process variant a) can be illustrated by the following equation:

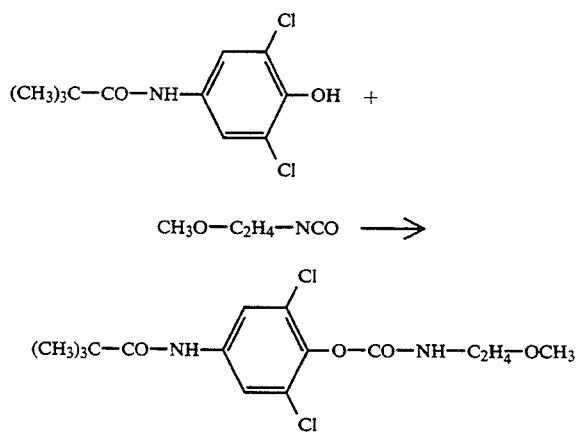

If, for example, 2,6-dichloro-4-(methyl-carbonylamino)phenol and N-methyl-N-(3,6-dioxaheptyl)-carbamoyl chloride are used as starting materials, the course of the reaction of process variant b) may be illustrated by the following equation:

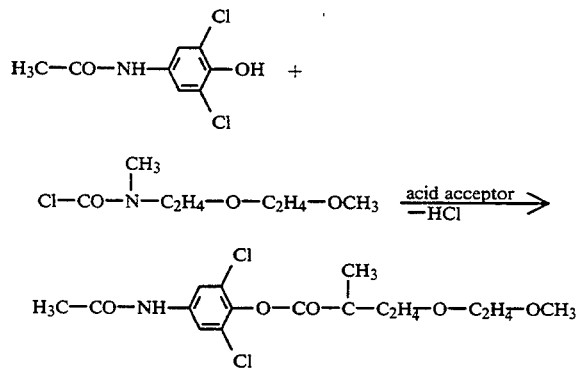

Formula (II) provides a general definition of the aminophenols required as starting materials for carrying out process variants a) and b) according to the invention. In this formula (II), the X and $Y^1$ to $Y^4$ radicals have the meanings which have already been given in connection with the description of the compounds of the formula (I) according to the invention. The majority of the compounds are known and can be prepared by analogous processes [cf. "Methoden der organischen Chemie" [Methods of organic chemistry] Houben-Weyl, Vol. VI/1C Phenols, Part 1, Georg Thieme Verlag Stuttgart (1976)].

Thus, for example, 4-amino-2-trifluoromethylphenyl is known from J. Org. Chem. 27, 4660 (1962); 4-amino-2-chloro- or -2-bromo-6-trifluoromethylphenols are known from Japanese Preliminary Published Specification Jp 61/126055, and, for example, 4-amino-2,3,5,6-tetrafluorophenol is known from Zh. Org. Khim. 10(9), 1923–1927 (1974). The compounds of the formula (IIA) or (IIB)

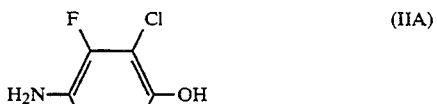

(IIA)

or

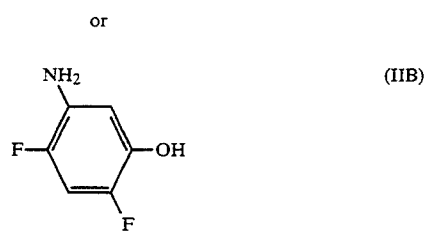

(IIB)

in which $Y^5$ represents fluorine or chlorine, which are still new, for example, can be prepared, for example, from appropriate hydroxybenzoic acids of the formula (VA) or (VB) respectively

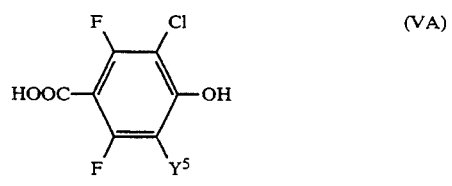

(VA)

or

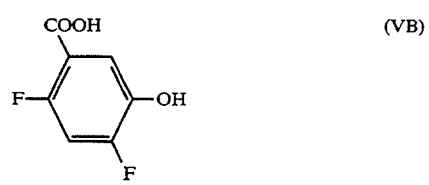

(VB)

by decarboxylation, and the resultant phenols of the formulae (VIA) or (VIB) respectively

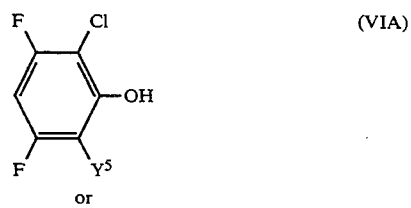

(VIA)

or

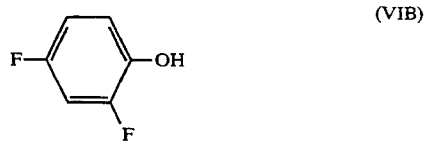

(VIB)

are nitrated to give the nitro compounds of the formula (VIIA) or (VIIB) respectively

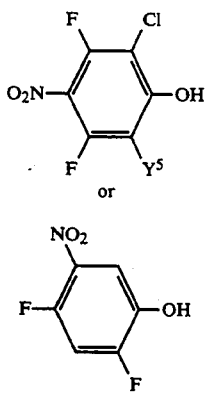

(VIIA)

or (VIIB)

which are then hydrogenated, for example using hydrogen and Raney nickel, to give the corresponding amines of the formulae (IIA) and (IIB).

The compounds of the formulae (VIIA) and (VIIB) are also compounds according to the invention.

Formula (III) provides a general definition of the isocyanates which are additionally required for carrying out process variant a) according to the invention. In this formula (III), the radicals $R^2$ to $R^7$, n and Z have the meanings which have already been given in connection with the description of the compounds of the formula (I) according to the invention. The compounds are known and can be prepared by analogous processes [cf. "Methoden der organischen Chemie" [Methods of organic chemistry] Houben-Weyl, Vol. E4, Carbonic acid derivatives, Georg Thieme Verlag Stuttgart, New York, pp. 738 ff (1983)].

The formula (IV) provides a general definition of the halogenocarbonyl compounds furthermore required for carrying out process variant b) according to the invention. In this formula (IV), the radicals Hal, $R^1$ to $R^7$, n and Z have the meanings which have already been given in connection with the description of the compounds of the formula (I) according to the invention.

The majority of the compounds of the formula (IV) are known or can be prepared by analogous processes [cf. "Methoden der organischen Chemie" [Methods of organic chemistry] Houben-Weyl, Vol. E4, Carbonic acid derivatives, Georg Thieme Verlag Stuttgart, New York, pp. 36 ff (1983)].

Suitable diluents for carrying out process variants a) and b) according to the invention are virtually all inert organic diluents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl and dibutyl ether, glycol dimethyl ether and diglycol dimethyl ether, tetrahydrofuran and dioxane, ketones, such as acetone, methyl ethyl, methyl isopropyl and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric trianide.

Process variants a) and b) according to the invention are generally carried out at temperatures between −50° C. and 120° C. The range between 0° C. and 110° C. is preferred. The reactions are generally carried out at atmospheric pressure.

Process variant b) is carried out, if appropriate, in the presence of acid acceptors. Acid acceptors which can be used are all conventional acid-binding agents. Alkali metal carbonates and alkali metal alcoholales, such as sodium carbonate, potassium carbonate, sodium methylate and ethylate, potassium methylate and ethylate, furthermore aliphatic, aromatic or heterocyclic amines, for example triethylamine, trimethylamine, dimethylaniline, 1,8-diazabicyclo(5,4,0)-undec-7-ene, dimethylbenzylamine and pyridine, have proved particularly successful.

Process variant a) is carried out, if appropriate, in the presence of a base. All bases which are cited as acid acceptors can be used.

To carry out process variant a) according to the invention, 1 to 2 mols, in particular 1 to 1.4 mols, of the compounds of the general formula (III) are preferably employed per mol of the phenol of the general formula (II).

To carry out process variant b) according to the invention, 1 to 2 mols, in particular 1 to 1 to 4 mols, of the compounds of the formula (IV) are preferably employed per mol of phenol of the general formula (II).

Work-up takes place by conventional methods, for example through extraction of the products from the water-diluted reaction mixture using toluene or methylene chloride, washing the organic phase with water, drying the organic phase, and distillation or so-called "incipient distillation" of the product, i.e. relatively lengthy heating to moderately elevated temperatures under reduced pressure in order to free the product of the final volatile components, or through chromatographic purification on silica gel or through crystallization. The refractive index, melting point, $R_f$ value or boiling point are used to characterize the compounds.

The active compounds according to the invention have a strong action against pests and can be employed in practice for combating undesired harmful organisms. The active compounds are suitable for use, in particular, as fungicides.

Fungicidal agents in plant protection are employed, for example, for combating Plasmodiophoromycetes, Oomycetes, Chytridiomycetes, Zygomycetes, Ascomycetes, Basidiomycetes and Deuteromycetes.

Bactericidal agents are employed in plant protection, for example for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora*; Pythium species, such as, for example, *Pythium ultimum*; Phyto-phthora species, such as, for example, *Phytophthora infes-tans*; Pseudoperonospora species, such as, for example, *Pseudoperonospora humuli* or *Pseudoperonospora cubensis*; Plasmopara species, such as, for example, *Plasmopara viti-cola*; Peronospora species, such as, for example, *Perono-spora pisi* or *P. brassicae*; Erysiphe species, such as, for example, *Erysiphe graminis*; Sphaerotheca species, such as, for example, *Sphaerotheca fuliginea*; Podosphaere species, such as, for example, *Podosphaera leucotricha*; Venturia species, such as, for example. *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-Low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

Example 1

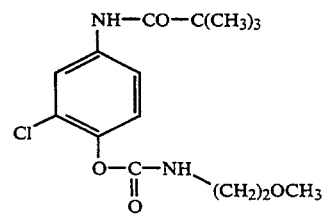

10 g (0.038 mol) of 2-chloro-4-(tert.-butyl-carbonylamino)-phenol are dissolved in 20 ml of toluene, and 4.2 g (0.042 mol) of 2-methoxyethyl isocyanate are added. 30 mg (0.2 mmol) of 1,8-diazabicyclo-(5,4,0)-undec-7-ene are subsequently added to the well-stirred reaction mixture. When the exothermic reaction (to 45° C.) has subsided, the mixture is stirred for a further 2 hours at 20° C. and cooled to 0° C., and the precipitated solid is filtered off under suction. The solid is subsequently taken up again in toluene:acetone=7:3 and filtered through silica gel using the same eluent. After evaporation of the solvents, 11.2 g (90% of theory) of 2-chloro-4-(tert.-butylcarbonylamino)-phenyl 2-methoxyethylcarbamate of melting point 118° C. are obtained.

The following are prepared analogously:

TABLE 1

$$X-NH-\underset{\underset{Y^4}{|}}{\overset{\overset{Y^1}{|}}{\bigcirc}}\underset{\underset{Y^3}{|}}{\overset{\overset{Y^2}{|}}{\bigcirc}}-O-CO-N-\underset{R^1}{\overset{R^2}{|}}C-\underset{R^3}{\overset{R^4}{|}}C-\underset{R^5}{\overset{R^6}{|}}(C)_{\overline{n}}OZ$$
$$\phantom{X-NH-}\phantom{xxxxxxxxxxxxxxxxxxxxx}R^1\phantom{xx}R^3\phantom{xx}R^5\phantom{xx}R^7$$

| Example No. | X | $Y^1$ | $Y^2$ | $Y^3$ | $Y^4$ | $R^1$ | $-\underset{R^3}{\overset{R^2}{\mid}}C-\underset{R^5}{\overset{R^4}{\mid}}C-\underset{R^7}{\overset{R^6}{\mid}}(C)_{\overline{n}}OZ$ | Physical data: *Rf value: silica gel 60F254; (Merck) eluent; toluene:acetone = 7:3; refractive index $n_D^{20}$; melting point °C. |
|---|---|---|---|---|---|---|---|---|
| 2 | —COC$_4$H$_9$-tert. | H | Cl | Cl | H | H | —CH$_2$CH$_2$OCH$_2$CH$_2$OCH$_3$ | 100 |
| 3 | —COC$_4$H$_9$-tert. | H | Cl | H | H | H | —CH$_2$CH$_2$OCH$_2$CH$_2$OCH$_3$ | 67–73 |
| 4 | —COC$_4$H$_9$-tert. | Cl | H | H | H | H | —CH$_2$CH$_2$OCH$_2$CH$_2$OCH$_3$ | 0.45* |
| 5 | —COOC$_2$H$_5$ | H | Cl | H | H | H | —CH$_2$CH$_2$OCH$_2$CH$_2$OCH$_3$ | 1.5290 |
| 6 | —COOC$_4$H$_9$-sek. | H | H | H | H | H | —CH$_2$CH$_2$OCH$_2$CH$_2$OCH$_3$ | 54–55 |
| 7 | —COOC$_3$H$_7$-i | H | CH$_3$ | H | H | H | —CH$_2$CH$_2$OCH$_2$CH$_2$OCH$_3$ | 74–76 |
| 8 | —COOC$_2$H$_5$ | H | CH$_3$ | H | H | H | —CH$_2$CH$_2$OCH$_2$CH$_2$OCH$_3$ | 57–58 |
| 9 | —COOC$_2$H$_5$ | H | Cl | Cl | H | H | —CH$_2$CH$_2$OCH$_2$CH$_2$OCH$_3$ | 1.529 |
| 10 | —COOC$_3$H$_7$-i | H | Cl | Cl | H | H | —CH$_2$CH$_2$OCH$_2$CH$_2$OCH$_3$ | 1.527 |
| 11 | —COOCH$_2$—C$_6$H$_5$ | H | Cl | Cl | H | H | —CH$_2$CH$_2$OCH$_2$CH$_2$OCH$_3$ | 76–80 |
| 12 | H | H | Cl | Cl | H | H | —CH$_2$CH$_2$OCH$_2$CH$_2$OCH$_3$ | 0.36* |
| 13 | —CO—NHCH$_2$—C(CH$_3$)$_3$ | H | Cl | H | H | H | —CH$_2$CH$_2$OCH$_2$CH$_2$OCH$_3$ | 129–131 |
| 14 | —CO—NH—C$_6$H$_4$—CF$_3$ | H | Cl | Cl | H | H | —CH$_2$CH$_2$OCH$_2$CH$_2$OCH$_3$ | 136–139 |
| 15 | —CO—NHCH$_3$ | H | Cl | Cl | H | H | —CH$_2$CH$_2$OCH$_2$CH$_2$OCH$_3$ | 190–191 |
| 16 | —SO$_2$—C$_6$H$_4$—CH$_3$ | H | Cl | Cl | H | H | —CH$_2$CH$_2$OCH$_2$CH$_2$OCH$_3$ | 176 |
| 17 | —CO—C(CH$_3$)(cyclopropyl) | H | Cl | Cl | H | H | —CH$_2$CH$_2$OCH$_2$CH$_2$OCH$_3$ | 0.44* |
| 18 | —CO—CH$_3$ | H | Cl | H | H | H | —CH$_2$CH$_2$OCH$_2$CH$_2$OCH$_3$ | 1.532* |
| 19 | —CO—CH$_3$ | H | Cl | H | H | H | —CH$_2$CH$_2$OCH$_2$CH$_2$OCH$_3$ | 128 |
| 20 | —CO—C$_6$H$_4$—Cl | H | Cl | Cl | H | H | —CH$_2$CH$_2$OCH$_2$CH$_2$OCH$_3$ | 0.47* |
| 21 | —CO—C$_4$H$_9$-tert. | H | Br | CF$_3$ | H | H | —CH$_2$CH$_2$OCH$_2$CH$_2$OCH$_3$ | 0.53* |
| 22 | —CO—C$_4$H$_9$-tert. | H | CF$_3$ | H | H | H | —CH$_2$CH$_2$OCH$_2$CH$_2$OCH$_3$ | 0.39* |
| 23 | —CO—C$_4$H$_9$-tert. | Cl | Cl | H | H | H | —CH$_2$CH$_2$OCH$_2$CH$_2$OCH$_3$ | 63–65 |
| 24 | —CO(CH$_2$)$_{16}$CH$_3$ | H | Cl | Cl | H | H | —CH$_2$CH$_2$OCH$_2$CH$_2$OCH$_3$ | 47 |
| 25 | —CO—C(CH$_3$)$_2$—C$_3$H$_7$-n | H | Cl | Cl | H | H | —CH$_2$CH$_2$OCH$_2$CH$_2$OCH$_3$ | 62–64 |

TABLE 1-continued

Structure:
$$X-NH-\text{(phenyl with }Y^1, Y^2, Y^3, Y^4\text{)}-O-CO-N(R^1)-C(R^2)(R^3)-C(R^4)(R^5)-(C(R^6)(R^7))_n-OZ$$

Physical data:
*Rf value: silica gel 60F254; (Merck) eluent; toluene:acetone = 7:3; refractive index $n_D^{20}$; melting point °C.

| Example No. | X | $Y^1$ | $Y^2$ | $Y^3$ | $Y^4$ | $R^1$ | $-C(R^2)(R^3)-C(R^4)(R^5)-(C(R^6)(R^7))_n-OZ$ | Physical data |
|---|---|---|---|---|---|---|---|---|
| 26 | $-CO-C(CH_3)(C_2H_5)-C_2H_5$ | H | Cl | Cl | H | H | $-CH_2CH_2OCH_2CH_2OCH_3$ | 66–67 |
| 27 | $-CO-$(1-methylcyclohexyl) | H | Cl | Cl | H | H | $-CH_2CH_2OCH_2CH_2OCH_3$ | 87–89 |
| 28 | $-CO-C(CH_3)(CH_2F)-CH_2F$ | H | Cl | Cl | H | H | $-CH_2CH_2OCH_2CH_2OCH_3$ | 80–82 |
| 29 | $-CO-C(CH_3)(CH_3)-CH_2Cl$ | H | Cl | Cl | H | H | $-CH_2CH_2OCH_2CH_2OCH_3$ | 72–75 |
| 30 | $-CO-C(CH_3)_2-$(3,4-dichlorophenyl) | H | Cl | Cl | H | H | $-CH_2CH_2OCH_2CH_2OCH_3$ | 0.56* |
| 31 | $-CO-$(1-methyl-4-isopropylcyclohexyl) | H | Cl | Cl | H | H | $-CH_2CH_2OCH_2CH_2OCH_3$ | 0.57* |
| 32 | $-CO-C(Cl)=CCl_2$ | H | Cl | Cl | H | H | $-CH_2CH_2OCH_2CH_2OCH_3$ | 1.516 |
| 33 | $-CO-OC_3H_7$-i | Cl | Cl | H | H | H | $-CH_2CH_2OCH_2CH_2OCH_3$ | 98 |
| 34 | $-CO-OC_2H_5$ | Cl | Cl | H | H | H | $-CH_2CH_2OCH_2CH_2OCH_3$ | 95 |
| 35 | $-CO-C_4H_9$-tert. | Cl | Cl | H | H | $CH_3$ | $-CH_2CH_2OCH_2CH_2OCH_3$ | 1.5265 |
| 36 | $-CO-$(1-methylcyclohexyl) | H | Cl | Cl | H | H | $-CH_2CH_2CH_2OCH_3$ | 136 |
| 37 | $-CO-$(1-methylcyclohexyl) | H | Cl | Cl | H | H | $-CH_2CH_2CH_2OC_4H_9$-n | 105 |
| 38 | $-CO-$(1-methylcyclohexyl) | H | Cl | Cl | H | H | $-CH_2CH_2OCH_2CH_2OC_4H_9$-n | 84 |

TABLE 1-continued

Structure:

X—NH—[benzene ring with Y¹, Y², Y³, Y⁴]—O—CO—N(R¹)—C(R²)(R³)—C(R⁴)(R⁵)—(C(R⁶)(R⁷))ₙ—OZ

| Example No. | X | Y¹ | Y² | Y³ | Y⁴ | R¹ | $-\underset{R^3}{\overset{R^2}{C}}-\underset{R^5}{\overset{R^4}{C}}-(\underset{R^7}{\overset{R^6}{C}})_{\overline{n}}OZ$ | Physical data: *Rf value: silica gel 60F254; (Merck) eluent; toluene:acetone = 7:3; refractive index $n_D^{20}$; melting point °C. |
|---|---|---|---|---|---|---|---|---|
| 39 | —CO—OC₄H₉-i | Cl | H | H | H | H | —CH₂CH₂OCH₂CH₂OCH₃ | 1.5186 |
| 40 | —CO—[1-methylcyclohexyl] | H | Cl | Cl | H | H | —CH₂CH₂CH₂OC₂H₅ | 138–141 |
| 41 | —CO—[1-methylcyclohexyl] | H | Cl | Cl | H | H | —CH₂CH₂OCH₃ | 130 |
| 42 | —CO—OC₂H₅ | Cl | H | H | H | H | —CH₂CH₂OCH₂CH₂OCH₃ | 1.5328 |
| 43 | —CO—[3-methylcyclohexyl] | H | Cl | Cl | H | H | —CH₂CH₂OCH₃ | 79 |
| 44 | —CO—[2-methyltetrahydropyran-2-yl] | H | Cl | Cl | H | H | —CH₂CH₂OCH₃ | 129–132 |
| 45 | —CO—[1-methylcyclohexyl] | H | CF₃ | Cl | H | H | —CH₂CH₂OCH₃ | 114 |
| 46 | —CO—C₄H₉-tert. | Cl | Cl | H | H | H | —CH₂CH₂OCH₃ | 68–69 |
| 47 | —CO—C(CH₃)(CH₂F)(CH₂F) | H | H | Cl | H | H | —CH₂CH₂OCH₃ | 122 |
| 48 | —CO—C(CH₃)(CH₃)(CH₂Cl) | H | Cl | Cl | H | H | —CH₂CH₂OCH₃ | 135 |
| 49 | —CO—C(CH₃)(C₂H₅)(C₂H₅) | H | Cl | Cl | H | H | —CH₂CH₂OCH₃ | 106–109 |
| 50 | —CO—[1-methylcyclohexyl] | F | Cl | Cl | F | H | —CH₂CH₂OCH₃ | |

TABLE 1-continued $$X-NH-\underset{Y^4}{\overset{Y^1}{\underset{Y^3}{\bigcirc}}}\overset{Y^2}{-}O-CO-\underset{R^1}{\overset{R^2}{N-\underset{R^3}{C}}}\overset{R^4}{\underset{R^5}{-C-}}\overset{R^6}{\underset{R^7}{(C)_n}}OZ$$

| Example No. | X | $Y^1$ | $Y^2$ | $Y^3$ | $Y^4$ | $R^1$ | $-\underset{R^3}{\overset{R^2}{C}}-\underset{R^5}{\overset{R^4}{C}}-\underset{R^7}{\overset{R^6}{(C)_n}}OZ$ | Physical data: *Rf value: silica gel 60F254; (Merck) eluent; toluene:acetone = 7:3; refractive index $n_D^{20}$; melting point °C. |
|---|---|---|---|---|---|---|---|---|
| 51 | cyclohexyl-CO- with CH3 | H | Cl | H | H | H | —CH₂CH₂OCH₃ | 100 |
| 52 | cyclohexyl-CO- with CH3 | H | Cl | H | H | H | CH(CH₃)CH₂OCH₃ | 88 |
| 53 | cyclohexyl-CO- with CH3 | Cl | Cl | H | H | H | —CH₂CH₂OCH₃ | 1.5430 |
| 54 | cyclohexyl-CO- | H | Cl | Cl | H | H | —CH₂CH₂OCH₃ | 156 |
| 55 | CO—C(CH₃)₂—OCH₃ | H | Cl | Cl | H | H | —CH₂CH₂OCH₃ | 115 |
| 56 | CO—C(OCH₃)₂(CH₃) | H | Cl | Cl | H | H | —CH₂CH₂OCH₃ | 102 |
| 57 | CO—C(CH₃)₂—CH₂OCH₃ | H | Cl | Cl | H | H | —CH₂CH₂OCH₃ | 80 |
| 58 | cyclohexyl-CO- with CH3 | F | F | Cl | F | H | —CH₂CH₂OCH₃ | 148 |
| 59 | cyclohexyl-CO- with CH3 | H | Cl | Cl | H | H | —CH(CH₃)CH₂OC₃H₇₋ᵢ | 96 |
| 60 | cyclohexyl-CO- with CH3 | H | Cl | Cl | H | H | CH(CH₃)CH₂OC₄H₉₋ₙ | 76 |
| 61 | cyclohexyl-CO- with CH3 | H | Cl | Cl | H | H | CH(C₂H₅)CH₂OCH₃ | 108 |

TABLE 1-continued

Structure:
$X-NH-\text{(phenyl with }Y^1, Y^2, Y^3, Y^4\text{)}-O-CO-N(R^1)-C(R^2)(R^3)-C(R^4)(R^5)-(C(R^6)(R^7))_n-OZ$ Physical data:
*Rf value: silica gel 60F254; (Merck) eluent; toluene:acetone = 7:3; refractive index $n_D^{20}$; melting point °C.

| Example No. | X | $Y^1$ | $Y^2$ | $Y^3$ | $Y^4$ | $R^1$ | $-C(R^2)(R^3)-C(R^4)(R^5)-(C(R^6)(R^7))_n-OZ$ | Physical data |
|---|---|---|---|---|---|---|---|---|
| 62 | 1-methylcyclohexyl-CO- | H | Cl | Cl | H | H | CH(CH₃)CH₂OCH(CH₃)C₂H₅ | 108 |
| 63 | 4-chlorophenyl-CO- | H | Cl | Cl | H | H | CH₂CH₂OCH₃ | 85 |
| 64 | 1-methylcyclohexyl-CO- | H | Cl | Cl | H | H | CH(CH₃)CH₂OC₃H₇-n | 110 |
| 65 | 1-methylcyclohexyl-CO- | H | Cl | Cl | H | H | CH(CH₃)CH₂OC₂H₅ | 107 |
| 66 | 1-methylcyclohexyl-CO- | H | Cl | Cl | H | H | CH(CH₃)CH₂OCH₃ | 83 |
| 67 | 1-methylcyclohexyl-CO- | H | CH₃ | H | H | H | CH₂CH₂OCH₃ | 115 |
| 68 | 1-methylcyclohexyl-CO- | H | Cl | Cl | H | H | CH₂CH₂OCH₂CH₂OCH₂CH₂OCH₃ | 61 |
| 69 | 1-methylcyclohexyl-CO- | H | Cl | H | H | H | CH(CH₃)CH₂OCH₃ | 88 |
| 70 | 1-methylcyclohexyl-CO- | H | Cl | Cl | H | H | CH₂CH₂OCH₃ | 103 |
| 71 | 1-methylcyclohexyl-CO- | H | Cl | Cl | H | H | CH(CH₃)CH₂OCH₂C(CH₃)₃ | 114 |
| 72 | 2-methyl-1,3-dioxolan-2-yl-CO- | H | Cl | Cl | H | H | CH₂CH₂OCH₃ | 102 |

TABLE 1-continued $$X-NH-\underset{Y^4}{\overset{Y^1}{\underset{|}{\bigcirc}}}\underset{Y^3}{\overset{Y^2}{\underset{|}{\bigcirc}}}-O-CO-N-\underset{R^1}{\overset{R^2}{\underset{|}{C}}}-\underset{R^3}{\overset{R^4}{\underset{|}{C}}}-(\underset{R^5}{\overset{R^6}{\underset{|}{C}}})_n OZ$$

| Example No. | X | $Y^1$ | $Y^2$ | $Y^3$ | $Y^4$ | $R^1$ | $-\underset{R^3}{\overset{R^2}{\underset{|}{C}}}-\underset{R^5}{\overset{R^4}{\underset{|}{C}}}-(\underset{R^7}{\overset{R^6}{\underset{|}{C}}})_n OZ$ | Physical data: *Rf value: silica gel 60F254; (Merck) eluent; toluene:acetone = 7:3; refractive index $n_D^{20}$; melting point °C. |
|---|---|---|---|---|---|---|---|---|
| 73 | CO-C(C₂H₅)(CH₂O-)(CH₂O-) (dioxane) | H | Cl | Cl | H | H | CH₂CH₂OCH₃ | 71 |
| 74 | CO-C(C₂H₅)(CH₂O-)(CH₂O-) | H | Cl | Cl | H | H | CH(CH₃)CH₂OCH₃ | 50 |
| 75 | CO-C(CH₃)(CH₂O-)(CH₂O-) | H | Cl | Cl | H | H | CH(CH₃)CH₂OCH₃ | 61 |
| 76 | CO-C(CH₃)(cyclohexyl) | H | Cl | Cl | H | H | CH₂C(CH₃)₂OCH₃ | 129 |
| 77 | CO-C(CH₃)(cyclohexyl) | H | Cl | H | H | H | CH₂C(CH₃)₂OCH₃ |  |
| 78 | CO-C(CH₃)(cyclohexyl) | H | Cl | Cl | H | H | C(CH₃)₂CH₂OCH₃ |  |
| 79 | CO-C(CH₃)(cyclohexyl) | H | Cl | H | H | H | C(CH₃)₂CH₂OCH₃ |  |
| 80 | CO-C(CH₃)(cyclohexyl) | H | Cl | Cl | H | H | CH(C₄H₉-t)CH₂OCH₃ |  |

TABLE 2

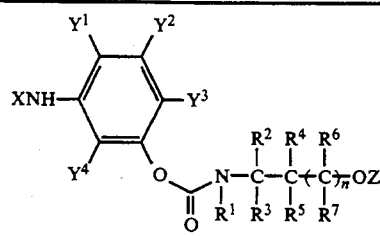

| Example No. | X | $Y^1$ | $Y^2$ | $Y^3$ | $Y^4$ | $R^1$ | $-\underset{R^3}{\overset{R^2}{C}}-\underset{R^5}{\overset{R^4}{C}}-(\underset{R^7}{\overset{R^6}{C}})_n OZ$ | Physical data: *Rf value: silica gel 60F254; (Merck); eluent; toluene:acetone = 7:3; refractive index $n_D^{20}$; melting point °C. |
|---|---|---|---|---|---|---|---|---|
| 81 | CO—cyclopropyl—CH₃ | F | H | Cl | H | H | CH₂CH₂OCH₂CH₂OCH₃ | 1.5322 |
| 82 | CO—cyclohexyl—CH₃ | F | H | CH₃ | H | H | CH(C₂H₅)CH₂OCH₃ | 70 |
| 83 | CO—cyclohexyl—CH₃ | F | H | CH₃ | H | H | CH₂CH₂OCH₃ | 102 |
| 84 | CO—cyclohexyl—CH₃ | F | H | Cl | H | H | CH(CH₃)CH₂OCH₃ | 85 |
| 85 | CO—cyclohexyl—CH₃ | F | H | Cl | H | H | CH₂CH₂OCH₃ | 110 |
| 86 | CO—cyclopropyl—CH₃ | F | H | Cl | H | H | CH₂CH₂OCH₃ | 97 |

TABLE 3

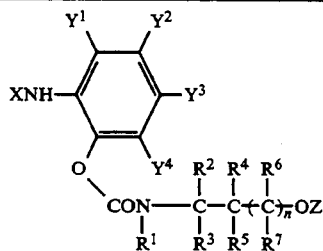

| Example No. | X | $Y^1$ | $Y^2$ | $Y^3$ | $Y^4$ | $R^1$ | $-\underset{R^3}{\overset{R^2}{C}}-\underset{R^5}{\overset{R^4}{C}}-(\underset{R^7}{\overset{R^6}{C}})_n OZ$ | Physical data: *Rf value: silica gel 60F254; (Merck); eluent; toluene:acetone = 7:3; refractive index $n_D^{20}$; melting point °C. |
|---|---|---|---|---|---|---|---|---|
| 87 | CO—cyclohexyl—CH₃ | H | Cl | H | H | H | CH₂CH₂OCH₃ | 94 |

TABLE 3-continued $$XNH-\overset{Y^1}{\underset{}{\bigcirc}}-Y^3$$

structure: aromatic ring with substituents XNH–, Y¹, Y², Y³, Y⁴, and O-CON(R¹)-C(R²)(R³)-C(R⁴)(R⁵)-(C(R⁶)(R⁷))ₙ-OZ

| Example No. | X | Y¹ | Y² | Y³ | Y⁴ | R¹ | $-\overset{R^2}{\underset{R^3}{C}}-\overset{R^4}{\underset{R^5}{C}}-(\overset{R^6}{\underset{R^7}{C}})_{\overline{n}}OZ$ | Physical data: *Rf value: silica gel 60F254; (Merck); eluent; toluene:acetone = 7:3; refractive index $n_D^{20}$; melting point °C. |
|---|---|---|---|---|---|---|---|---|
| 88 | CO—cyclohexyl-CH₃ | H | H | H | H | H | CH₂CH₂OCH₃ | 101 |
| 89 | CO—cyclohexyl-CH₃ | H | Cl | H | Cl | H | CH₂CH₂OCH₃ | 146 |
| 90 | COC(CH₃)₃ | H | C(CH₃)₃ | H | H | H | CH₂CH₂OCH₃ | 132 |
| 91 | COC(CH₃)₃ | H | F | H | H | H | CH₂CH₂OCH₃ | 104 |
| 92 | COC(CH₃)₃ | H | SO₂CH₃ | H | H | H | CH₂CH₂OCH₃ | *0.35 |
| 93 | CO—cyclohexyl-CH₃ | H | Cl | H | H | H | CH₂CH₂OCH₃ | 101 |

Preparation of the starting materials of the formula (III)

Example III

1. 2-Methoxy-ethyl isocyanate

1.1 Preparation of 2-ethylhexyl N-(2-methoxyethyl)-carbamate (corresponding to European Patent Specification 0,027,940)

225 g (3.0 mols) of 2-methoxyethylamine, 180 g (3.0 mols) of urea, 1,950 g (15 mols) of 2-ethylhexanol and 3 g of dibutyltin oxide are introduced into a 4 liter round-bottom flask equipped with reflux condenser, and the mixture is heated while stirring. A vigorous evolution of ammonia sets in at temperatures above 110° C. Ammonia gas is removed through the reflux condenser and absorbed in water. Over the course of 3 hours, the temperature is increased to 180° C. (reflux), the elimination of ammonia virtually ceasing. After a further 2 hours under reflux, the mixture is freed of remaining ammonia by flushing with nitrogen and subsequently subjected to fractional distillation. After a first cut comprising mainly ethylhexanol, the desired urethane distills over at 98°–100° C./0.1 mbar as a colorless liquid (yield: 617 g=89% of theory). 27 g of a brown liquid remain as the distillation residue and solidify to give a pasty product on cooling.

1.2 Thermal cleavage of 2-ethylhexyl N-(2-methoxyethyl)-carbamate (corresponding to EP 0,054,817)

The cleavage apparatus used is a round-bottom flask which is fitted with a dropping funnel and a stirrer and to which two reflux condensers, which are subjected to thermostatic control by means of heat-transfer oil, are attached one on top of the other. A withdrawal tray is located between the two reflux condensers.

The urethane is cleaved continuously without removing the residue.

pressure: 29 mbar
temperature: cleavage flask: 174–178° C.
  oil first cut of lower condenser: 135° C.
  oil first cut of upper condenser: 65° C.
average residence time: about 4 hours cleavage fractions:
  withdrawal tray: 70.1% by weight of ethylhexanol
  top of the upper condenser: 92.5% by weight of isocyanate When the cleavage is complete, the mixtures obtained are in each case subjected to fractional distillation.
Overall result of the cleavage:

urethane:  employed: 3.11 kg
  recovered: 0.84 kg
  reacted: 2.27 kg 2-methoxyethyl isocyanate, distilled: 920 g
(b.p. 124° C.), purity: 99.3% (GC)
→ selectivity: 92%

2-ethylhexanol: 1.23 kg
→ selectivity: 96%
residue: 114 g

Preparation of the starting materials for the preparation of the compounds of the formula (II), and compounds of the formula (II)

Example A1:

3,5-Dichloro-2,6-difluoro-4-hydroxybenzoic acid 300 g of potassium hydroxide, 600 ml of water, 15 g of tetrabutylammonium chloride and 135 g of 3,5-dichloro-2,4,6-trifluorobenzotrifluoride are introduced into a stirred apparatus and the mixture is then refluxed for 5 hours. When the reaction is complete, the mixture is cooled and acidified by dropwise addition of hydrochloric acid. The solid product is filtered off under suction and dried in vacuo. Yield: 93 g having a melting point of 102°–105° C.

Example A2:

3-Chloro-2,5,6-trifluoro-4-hydroxy-benzoic acid

From 400 g of NaOH, 1,200 ml of water, 15 g of tetraethylammonium chloride and 276 g of 3-chloro-tetrafluorobenzotrifluoride, 238 g of product of melting point 87°–90° C. are obtained analogously to Example A1 on refluxing for 6 hours.

Example A3:

2,6-Dichloro-3,5-difluorophenol 50 g of 3,5-dichloro-2,6-difluoro-4-hydroxy-benzoic acid and 10 ml of dimethylformamide are mixed and heated. At 105°–130° C., carbon dioxide evolves, and the reaction is allowed to run to completion at this temperature. 200 ml of toluene and then 80 ml of water are subsequently stirred into the mixture, the phases are separated, and the organic phase is dried and subsequently distilled. 34 g product of boiling point 87°–88° C. are obtained; $n_D^{20}$: 1.5310.

Example A4:

2-Chloro-3,5,6-trifluorophenol of boiling point 68°–70° C./20 mbar are obtained analogously to Example A3.

Example A5:

2,6-Dichloro-3,5-difluoro-4-nitro-phenol 20 g of 2,6-dichloro-3,5-difluorophenol are introduced into 70 ml of acetic acid, and 8 g of 98% strength nitric acid are added dropwise. The mixture is subsequently stirred for a further 2 hours at room temperature and taken up in 150 ml of dichloromethane, and the solution is washed twice with water. After removing the dichloromethane by distillation, 18 g of product remain. 94% purity according to GC analysis.

Example A6:

2-Chloro-3,5,6-trifluoro-4-nitrophenol 25 g of 2-chloro-3,5,6-trifluoro-4-nitrophenol of purity 93% and melting point 107°–109° C. are obtained from 28 g of 2-chloro-3,5,6-trifluorophenol by nitration analogously to Example A5.

Example A7:

2,6-Dichloro-3,5-difluoro-4-amino-phenol 18 g of 2,6-dichloro-3,5-difluoro-4-nitrophenol are hydrogenated in 100 ml of methanol in the presence of 1.5 g of Raney nickel at 25°–45° C. using 30-50 bar of hydrogen until the take-up of hydrogen is complete. After filtration, the solution is freed from solvent under reduced pressure. 13 g of aminophenol (GC purity 98.4%) remain; m.p. 151° C.

Example A8:

2-Chloro-3,5,6-trifluoro-4-amino-phenol

From 25 g of 2-chloro-3,5,6-trifluoro-4-nitrophenol in 120 ml of methanol and 2 g of Raney nickel, 20 g of aminophenol (GC purity 97%) are obtained by hydrogenation analogously to Example A7.

Example A9:

(2,4-Difluoro-5-nitro)-phenyl trifluorochloroethyl ether 150 g of potassium fluoride in 350 ml of tetramethylene sulphone are initially introduced and dried azeotropically using xylene. 200 g of (2,4-dichloro-5-nitro)-phenyl trifluorochloroethyl ether are then added, and the mixture is heated at 180° C. for 5 hours, and subsequently at 190°–195° C. for a further 5 hours with exclusion of moisture. After cooling, the batch is stirred into 1 liter of water and extracted repeatedly with toluene. The toluene phase is washed twice with water and then dried. 89 g of (2,4-Difluoro-5-nitro)-phenyl trifluorochloroethyl ether of boiling point 133°–37° C./16 mbar are obtained by distillation.

Example A10:

2,4-difluoro-5-nitrophenol 50 g of (2,4-difluoro-5-nitro)-phenyl trifluorochloroethyl ether and 25 ml of tetramethylene sulphone are initially introduced, and 50 ml of concentrated sulphuric acid and 0.5 g of iron(III) chloride are added. The mixture is then heated at 100° C. for 3 hours, and cooled, and 100 g of ice are added in order to subsequently reflux for a further 2 hours. After 250 ml of water had been stirred in, the product was extracted repeatedly with toluene, and the toluene phase was dried and distilled. 24 g of 2,4-difluoro-5-nitrophenol are obtained.

Boiling point: 160°–162° C./24 mbar, m.p. 117°–119° C.

Example A11:

2,4-difluoro-5-amino-phenol 24 g of 2,4-Difluoro-5-nitrophenol, dissolved in 120 ml of methanol, are subjected to hydrogenation at a hydrogen pressure of 20–40 bar at 25°–45° C. in the presence of 2 g of Raney nickel. When constant pressure is reached (i.e. when the take-up of hydrogen is complete), the pressure is released and the mixture is cooled, the solution is free from catalyst by filtration, and the methanol is subsequently removed by distillation at reduced pressure. 18 g (GC purity 97.5%) of 2,4-difluoro-5-aminophenol are obtained.

Example A

Botrytis test (bean)/protective

Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

The compounds of preparation Examples 39 and 42, for example, show at 50 ppm an infection degree of 5%.

Example B

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

The compounds of preparation Examples 6, 10, 14, 15, 18, 19, 21, 23, 27 and 28, for example, show at a compound concentration of 0.025% an infection degree of 0 to 10%.

It will be understood that the specification and examples are illustrative but not limitative of the present invention and that other embodiments within the spirit and scope of the invention will suggest themselves to those skilled in the art.

We claim:

1. A substituted aminophenyl carbamate of the formula (I):

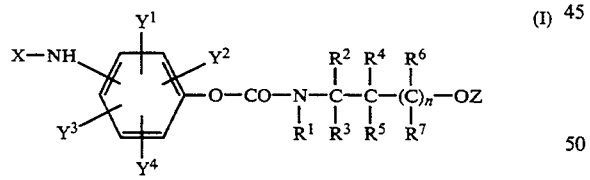

wherein

X represents, with the exception of alkoxycarbonyl and cycloalkylcarbonyl, $-CO-OR^9$; $-CO-SR^9$; $-CO-R^{10}$; $-SO_2R^9$; or hydrogen; in which $R^9$ represents aryl, which is optionally monosubstituted to polysubstituted by identical or different substituents selected from the group consisting of halogen, alkyl having 1 to 6 carbon atoms, alkoxy having 1 to 6 carbon atoms, alkylthio having 1 to 6 carbon atoms, halogenoalkyl having 1 to 6 carbon atoms and 1 to 9 identical or different halogen atoms, halogenoalkoxy having 1 to 6 carbon atoms and 1 to 9 identical or different halogen atoms, halogenoalkylthio having 1 to 6 carbon atoms and 1 to 9 identical or different halogen atoms, cyano and nitro; or represents aralkyl, which is optionally monosubstituted to polysubstituted by identical or different substituents selected from the group consisting of halogen, alkyl having 1 to 6 carbon atoms, alkoxy having 1 to 6 carbon atoms, alkylthio having 1 to 6 carbon atoms, halogenoalkyl having 1 to 6 carbon atoms and 1 to 9 identical or different halogen atoms, halogenoalkoxy having 1 to 6 carbon atoms and 1 to 9 identical or different halogen atoms, halogenoalkylthio having 1 to 6 carbon atoms and 1 to 9 identical or different halogen atoms, cyano and nitro; or represents alkyl; or represents alkyl, which is monosubstituted to tetrasubstituted by identical or different substituents selected from the group consisting of halogen, alkoxy, or alkylthio; or represents alkenyl; or represents halogenoalkenyl; or represents cycloalkyl or cycloalkylalkyl, each of which is optionally monosubstituted to polysubstituted by identical or different substituents selected from the group consisting of halogen, alkyl having 1 to 6 carbon atoms, and halogenoalkyl having 1 to 6 carbon atoms and 1 to 9 identical or different halogen atoms; or represents cycloalkenyl, which is optionally monosubstituted or polysubstituted by identical or different alkyl having 1 to 6 carbon atoms; and $R^{10}$ represents aryl, which is optionally monosubstituted to polysubstituted by identical or different substituents selected from the group consisting of halogen, alkyl having 1 to 6 carbon atoms, alkoxy having 1 to 6 carbon atoms, alkylthio having 1 to 6 carbon atoms, halogenoalkyl having 1 to 6 carbon atoms and 1 to 9 identical or different halogen atoms, halogenoalkoxy having 1 to 6 carbon atoms and 1 to 9 identical or different halogen atoms, halogenoalkylthio having 1 to 6 carbon atoms and 1 to 9 identical or different halogen atoms, cyano and nitro; or represents aralkyl, which is optionally monosubstituted to polysubstituted by identical or different substituents selected from the group consisting of halogen, alkyl having 1 to 6 carbon atoms, alkoxy having 1 to 6 carbon atoms, alkylthio having 1 to 6 carbon atoms, halogenoalkyl having 1 to 6 carbon atoms and 1 to 9 identical or different halogen atoms, halogenoalkoxy having 1 to 6 carbon atoms and 1 to 9 identical or different halogen atoms, halogenoalkylthio having 1 to 6 carbon atoms and 1 to 9 identical or different halogen atoms, cyano and nitro; or represents alkyl, which is optionally monosubstituted to tetrasubstituted by identical or different substituents selected from the group consisting of halogen, alkoxy, or alkylthio; or represents alkenyl; or represents halogenoalkenyl; or represents cycloalkyl or cycloalkylalkyl; or represents cycloalkyl or cycloalkylalkyl, each of which is monosubstituted to polysubstituted by identical or different substituents selected from the group consisting of halogen, alkyl having 1 to 6 carbon atoms, and halogenoalkyl having 1 to 6 carbon atoms and 1 to 9 identical or different halogen atoms; cycloalkenyl, which is optionally monosubstituted or polysubstituted by identical or different alkyl having 1 to 6 carbon atoms; or represents a heterocyclic ring, which is optionally monosubstituted to polysubstituted by identical or different alkyl having 1 to 6 carbon atoms;

$Y^1$ to $Y^4$ are identical or different and represent hydrogen; halogen; nitro; cyano; alkyl; halogenoalkyl; alkoxy; halogenoalkoxy; alkylthio; alkylsulfonyl; or halogenoalkylthio;

$R^1$ to $R^7$ are identical or different and represent hydrogen; alkyl; halogenoalkyl; or alkoxyalkyl;

n represents 0 or 1; and

Z represents alkyl; halogenoalkyl; or a radical having the formula:

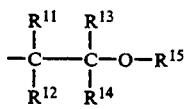

in which $R^{11}$ to $R^{14}$ are identical or different and represent hydrogen; alkyl; halogenoalkyl; or alkoxyalkyl; and $R^{15}$ represents alkyl; halogenoalkyl; or alkoxyalkyl.

2. A substituted aminophenyl carbamate according to claim 1, in which

X represents —CO—OR$^9$; —CO—SR$^9$; —CO—R$^{10}$; —SO$_2$R$^9$ or hydrogen, with the exception of alkoxycarbonyl and cycloalkylcarbonyl, in which R$^9$ represents aryl having 6 to 12 carbon atoms, aryl having 6 to 12 carbon atoms which is monosubstituted to hexasubstituted by identical or different substituents from the group consisting of halogen, alkyl having 1 to 6 carbon atoms, alkoxy having 1 to 6 carbon atoms, alkylthio having 1 to 6 carbon atoms, halogenoalkyl having 1 to 6 carbon atoms and 1 to 9 identical or different halogen atoms, halogenoalkoxy having 1 to 6 carbon atoms and 1 to 9 identical or different halogen atoms, halogenoalkylthio having 1 to 6 carbon atoms and 1 to 9 identical or different halogen atoms, cyano and nitro; or represents aralkyl having 6 to 12 carbon atoms in the aryl part and having 1 to 6 carbon atoms in the straight-chain or branched alkyl part, which is optionally monosubstituted to hexasubstituted by identical or different substituents from the group consisting of the abovementioned aryl substituents; or represents straight-chain or branched alkyl having 1 to 20 carbon atoms; or represents alkyl having 1 to 20 carbon atoms which is monosubstituted to tetrasubstituted by identical or different substituents from the group consisting of halogen, alkoxy having 1 to 6 carbon atoms and alkylthio having 1 to 6 carbon atoms, wherein each of the alkyl part is straight-chain or branched; or represents straight-chain or branched alkenyl having 2 to 16 carbon atoms or alkenyl having 2 to 6 carbon atoms which is monosubstituted to hexasubstituted by identical or different halogen; or represents cycloalkyl having 3 to 10 carbon atoms or cycloalkylalkyl having 1 to 10 carbon atoms in the straight-chain or branched alkyl part and 3 to 10 carbon atoms in the cycloalkyl part, each of which is optionally monosubstituted to hexasubstituted by identical or different substituents from the group consisting of halogen, straight-chain or branched alkyl having 1 to 6 carbon atoms and halogenoalkyl having 1 to 6 carbon atoms and 1 to 9 identical or different halogen atoms; represents cycloalkenyl which has 5 to 10 carbon atoms and which may be monosubstituted to hexasubstituted by identical or different, straight-chain or branched alkyl having 1 to 6 carbon atoms;

R$^{10}$ has the meaning of R$^9$ or represents a 6-membered heterocyclic ring which contains one or two oxygen atoms, and which may be monosubstituted to hexasubstituted by identical or different, straight-chain or branched alkyl having 1 to 6 carbon atoms;

$Y^1$ to $Y^4$ are identical or different and represent hydrogen, halogen, nitro, cyano, straight-chain or branched alkyl having 1 to 6 carbon atoms, halogenoalkyl having 1 to 6 carbon atoms in the straight-chain or branched alkyl part and 1 to 9 identical or different halogen atoms, alkoxy or halogenoalkoxy, alkylthio, alkylsulfonyl or halogenoalkylthio in each case having 1 to 6 carbon atoms in the straight-chain or branched alkyl part, and if appropriate, 1 to 9 identical or different halogen atoms;

$R^1$ to $R^7$ are identical or different and represent hydrogen, straight-chain or branched alkyl having 1 to 6 carbon atoms, halogenoalkyl having 1 to 6 carbon atoms in the straight-chain or branched alkyl part and 1 to 9 identical or different halogen atoms, or alkoxyalkyl having 1 to 6 carbon atoms in each straight-chain or branched alkyl part;

n represents 0 or 1, and

Z represents straight-chain or branched alkyl or halogenoalkyl each having 1 to 6 carbon atoms and, if appropriate, 1 to 9 identical or different halogen atoms, or the

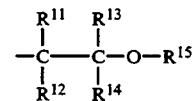

radical, in which $R^{11}$ to $R^{14}$ are identical or different and represent hydrogen, straight-chain or branched alkyl having 1 to 6 carbon atoms, halogenoalkyl having 1 to 6 carbon atoms in the straight-chain or branched alkyl part and 1 to 9 identical or different halogen atoms, or alkoxyalkyl having 1 to 6 carbon atoms in each straight-chain or branched alkyl part, and $R^{15}$ represents straight-chain or branched alkyl, alkoxyalkyl or halogenoalkyl each having 1 to 6 carbon atoms in each alkyl part and, if appropriate, 1 to 9 identical or different halogen atoms.

3. A substituted aminophenyl carbamate according to claim 1, in which

X represents —CO—OR$^9$; —CO—SR$^9$; —CO—R$^{10}$; —SO$_2$R$^9$ or hydrogen, with the exception of alkoxycarbonyl and cycloalkylcarbonyl, in which R$^9$ represents phenyl, benzyl, phenylethyl or 1-phenyl-1-methyl-ethyl each of which is optionally monosubstituted, disubstituted or trisubstituted in the phenyl part by identical or different substituents from the group consisting of halogen, straight-chain or branched alkyl having 1 to 4 carbon atoms, straight-chain or branched alkoxy having 1 to 4 carbon atoms, straight-chain or branched alkylthio having 1 to 4 carbon atoms, halogenoalkyl, halogenoalkoxy and halogenoalkylthio in each case having 1 to 4 carbon in the straight-chain or branched alkyl part and 1 to 5 identical or different halogen atoms, cyano and nitro; or represents straight-chain or branched alkyl having 1 to 18 carbon atoms; or represent straight-chain or branched alkyl having 1 to 18 carbon atoms which is monosubstituted, disubstituted or trisubstituted by identical or different substituents from the group consisting of halogen, alkoxy having 1 to 6 carbon atoms or alkylthio having 1 to 6 carbon atoms, wherein each of the alkyl parts is straight-chain or branched; or represents straight-chain or branched alkenyl having 2 to 8 carbon atoms; or represent straight-chain or branched alkenyl having 2 to 4 carbon atoms which is monosubstituted, disubstituted or trisubstituted by identical or different halogen; cycloalkyl which has 3 to 6 carbon atoms or cycloalkyl-alkyl which has 3 to 6 carbon atoms in the cycloalkyl part and 1 to 6 carbon atoms in the straight-chain or branched alkyl part and each of which is optionally monosubstituted, disubstituted or trisubstituted by identical or different substituents from the group consisting of halogen, straight-chain or branched alkyl having 1 to 4 carbon atoms and straight-chain or branched halogenoalkyl having 1 to 4 carbon atoms and 1 to 5 identical or different halogen atoms;

$R^{10}$ has the meaning of $R^9$ or represents a 6-membered heterocyclic ring which contains one or two oxygen atoms and which is optionally monosubstituted, disubstituted or trisubstituted by straight-chain or branched alkyl having 1 to 4 carbon atoms, $Y^1$ to $Y^4$ are identical or different and represent hydrogen, halogen, straight-chain or branched alkyl having 1 to 4 carbon atoms, straight-chain or branched alkoxy or alkylsulfonyl having each 1 to 4 carbon atoms, or halogenalkyl having 1 to 4 carbon atoms in the straight-chain or branched alkyl part and 1 to 5 identical or different halogen atoms;

$R^1$ to $R^7$ are identical or different and represent hydrogen or straight-chain or branched alkyl having 1 to 6 carbon atoms, n represents 0, and Z represents straight-chain or branched alkyl or halogenoalkyl each having 1 to 4 carbon atoms and, if appropriate, 1 to 5 identical or different halogen atoms, or the

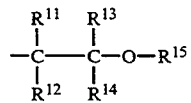

radical, in which $R^{11}$ to $R^{14}$ are identical or different and represent hydrogen, straight-chain or branched alkyl or halogenoalkyl in each case having 1 to 4 carbon atoms and, if appropriate, 1 to 5 identical or different halogen atoms and $R^{15}$ represents straight-chain or branched alkyl, alkoxyalkyl or halogenoalkyl in each case having 1 to 4 carbon atoms in each alkyl part and, if appropriate, 1 to 5 identical or different halogen atoms.

4. A substituted aminophenyl carbamate according to claim 1, in which

X represents —CO—OR$^9$; —CO—SR$^9$; —CO—R$^{10}$; —SO$_2$R$^9$ or hydrogen, with the exception of alkoxycarbonyl and cycloalkylcarbonyl, in which $R^9$ represents phenyl which is optionally monosubstituted, disubstituted or trisubstituted by identical or different substituents from the group consisting of methyl, ethyl, methoxy, ethoxy, trichloromethyl, trifluoromethyl, trichloromethoxy, trifluoromethoxy, fluorine and chlorine; or represents benzyl; or represents straight-chain or branched alkyl having 1 to 5 carbon atoms; or represents halogenoalkyl having 1 to 4 carbon atoms and 1 or 2 chlorine or fluorine atoms; or represents halogenoalkenyl having 2 or 3 carbon atoms and 1 to 4 chlorine atoms; or represents cyclopropyl or cyclohexyl each of which is optionally monosubstituted, disubstituted or trisubstituted by identical or different, straight-chain or branched alkyl having 1 to 4 carbon atoms, $R^{10}$ represents straight-chain or branched alkyl having 1 to 18 carbon atoms, or represents phenyl, cyclopropyl or cyclohexyl each of which is optionally monosubstituted, disubstituted or trisubstituted by identical or different substituents from the group consisting of methyl, ethyl, n-propyl, iso-propyl, chlorine or trifluoromethyl; or represents phenylalkyl which has 1 to 3 carbon atoms in the straight-chain or branched alkyl part and which is optionally monosubstituted or disubstituted by chlorine; or represents straight-chain or branched halogenoalkyl having 1 to 4 carbon atoms and 1 or 2 chlorine or fluorine atoms; or represents straight-chain or branched halogenoalkenyl having 2 to 4 carbon atoms and 1 to 4 identical or different halogen atoms, or represents oxyanyl or oxolanyl, dioxanyl or dioxolanyl each of which is optionally monosubstituted by methyl or ethyl;

$Y^1$ to $Y^4$ are identical or different and represent hydrogen, chlorine, fluorine, bromine, methyl, t-butyl trifluoromethyl or methylsulfonyl, $R^1$ to $R^7$ are identical or different and represent hydrogen or methyl, n represents 0, and Z represents straight-chain or branched alkyl having 1 to 4 carbon atoms, or the

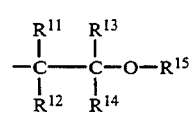

radical, in which $R^{11}$ to $R^{11}$ represent hydrogen, and $R^{15}$ represents methyl, ethyl, propyl, butyl, methoxyethyl or ethoxyethyl.

5. A fungicidal composition comprising a fungicidally effective amount of a substituted aminophenyl carbamate according to claim 1 and a diluent.

6. A method of combating fungi which comprises applying to such fungi or to a fungus habitat a fungicidally effective amount of a substituted aminophenyl carbamate according to claim 1.

* * * * *

UNITED STATES PATENT AND TRADEMARK OFFICE
CERTIFICATE OF CORRECTION

PATENT NO. : 5,371,271
DATED : December 6, 1994
INVENTOR(S) : Kruger, et al.

It is certified that error appears in the above-indentified patent and that said Letters Patent is hereby corrected as shown below:

| | |
|---|---|
| Title Page | ABSTRACT: Line 19 delete "halogenolkyl-thio " and substitute -- halogenoalkyl-thio -- |
| Col. 35, line 51 | Delete " part " and substitute -- parts -- |
| Col. 36, line 65 | After " carbon " insert -- atoms -- |
| Col. 38, line 35 | Delete " oxyanyl " and substitute -- oxanyl -- |
| Col. 38, line 53 | After " $R^{11}$ to " delete " $R^{11}$ " and substitute -- $R^{14}$ -- |

Signed and Sealed this

Second Day of June, 1998

Attest:

BRUCE LEHMAN

*Attesting Officer*    *Commissioner of Patents and Trademarks*